US007943782B2

(12) United States Patent
Henry

(10) Patent No.: US 7,943,782 B2
(45) Date of Patent: May 17, 2011

(54) CRYSTALLINE CHEMOTHERAPEUTIC

(75) Inventor: Rodger F. Henry, Wildwood, IL (US)

(73) Assignee: Abbott Laboratories, Abbott Park, IL (US)

( * ) Notice: Subject to any disclaimer, the term of this patent is extended or adjusted under 35 U.S.C. 154(b) by 81 days.

(21) Appl. No.: 12/251,964

(22) Filed: Oct. 15, 2008

(65) Prior Publication Data
US 2009/0105486 A1    Apr. 23, 2009

Related U.S. Application Data

(60) Provisional application No. 60/981,243, filed on Oct. 19, 2007.

(51) Int. Cl.
*C07D 231/56* (2006.01)
(52) U.S. Cl. .................................... 548/362.1
(58) Field of Classification Search .................. None
See application file for complete search history.

(56) References Cited

U.S. PATENT DOCUMENTS 7,297,709 B2   11/2007   Dai et al.

FOREIGN PATENT DOCUMENTS

WO   WO2004113304 A1   12/2004
WO   WO2007050574 A1   5/2007

OTHER PUBLICATIONS

Dai et al., Journal of Medicinal Chemistry, (2007), vol. 50, p. 1584-1597.*
U.S. Pharmacopoeia, pp. 1843-1884 (1995).
Dai, et al, "Discover of N-(4-(3-Amino-1H-indazol-4-yl)phenyl)-N'-(2-fluoro-5-methylphenyl)urea (ABT-869), a 3-Aminoindazole-Based Orally Active Multitargeted Receptor Tyrosine Kinase Inhibitor", J. Med. Chem., 50, 1584-1597 (2007).
International Search Report PCT, Jan. 27, 2009.
Aulton M.E., ed., Pharmaceutics: The Science of Dosage Form Design, 2nd Edition, Churchill Livingstone, 2004, Table of Contents.
Hilfiker R., ed., Polymorphism in the Pharmaceutical Industry, Wiley-VCH Verlag GmbH & Co., KGaA, Weinheim, Germany, 2006, Table of Contents.
Morris K.M., "Structural Aspects of Hydrate and Solvates," Polymorphism in Pharmaceutical Solids, 1999, pp. 125-181.
Spanish Minerals: X-rays and the Diffraction by Crystals, http://translate.googleusercontent.com/translate_c?hl=en&sl=es&u=http://www.spanishmi, (2010).

* cited by examiner

*Primary Examiner* — Yong Chu
(74) *Attorney, Agent, or Firm* — Glen Gesicki

(57) ABSTRACT

N-(4-(3-Amino-1H-indazol-4-yl)phenyl)-N'-(2-fluoro-5-methylphenyl)urea Tolueneate Crystalline Form 1, ways to make it and ways to use it are disclosed.

3 Claims, No Drawings

US 7,943,782 B2

CRYSTALLINE CHEMOTHERAPEUTIC

CROSS REFERENCE TO RELATED APPLICATIONS

The present application claims priority to U.S. Provisional Application Ser. No. 60/981,243, filed Oct. 19, 2007; hereby incorporated in its entirety by reference.

FIELD OF THE INVENTION

This invention pertains to N-(4-(3-Amino-1H-indazol-4-yl)phenyl)-N'-(2-fluoro-5-methylphenyl)urea Tolueneate Crystalline Form 1, ways to make it and ways to use it.

BACKGROUND OF THE INVENTION

N-(4-(3-Amino-1H-indazol-4-yl)phenyl)-N'-(2-fluoro-5-methylphenyl)urea (ABT-869) belongs to a family of protein tyrosine kinases (PTKs) which catalyze the phosphorylation of specific tyrosine residues in cellular proteins. Aberrant or excessive PTK activity has been observed in many disease states including benign and malignant proliferative disorders and diseases resulting from inappropriate activation of the immune system.

Crystallinity of solvates of ABT-869 may effect, among other physical and mechanical properties, their stability, solubility, dissolution rate, hardness, compressibility and melting point. Because ease of manufacture and formulation of ABT-869 is dependent on some, if not all, of these properties, there is an existing need in the chemical and therapeutic arts for identification of crystalline forms of ABT-869 and ways to reproducibly make them.

SUMMARY OF THE INVENTION

One embodiment of this invention, therefore, pertains to N-(4-(3-Amino-1H-indazol-4-yl)phenyl)-N'-(2-fluoro-5-methylphenyl)urea Tolueneate Crystalline Form 1 which, when measured at about −100° C. in the monoclinic crystal system and $P2_1/C$ space group with radiation at 0.7107 Å, is characterized by respective lattice parameter values a, b and c of 13.80 Å±0.001 Å, 8.910 Å±0.007 Å and 19.87 Å±0.02 Å and respective $\alpha$, $\beta$ and $\gamma$ values of about 90°, 103.75°±0.01° and 90°.

Another embodiment pertains to formulations made with an excipient and N-(4-(3-Amino-1H-indazol-4-yl)phenyl)-N'-(2-fluoro-5-methylphenyl)urea Tolueneate Crystalline Form 1 which, when measured at about −100° C. in the monoclinic crystal system and $P2_1/C$ space group with radiation at 0.7107 Å, is characterized by respective lattice parameter values a, b and c of 13.80 Å±0.01 Å, 8.910 Å±0.007 Å and 19.87 Å±0.02 Å and respective $\alpha$, $\beta$ and $\gamma$ values of about 90°, 103.75°±0.01° and 90°.

Still another embodiment pertains to a process for making N-(4-(3-Amino-1H-indazol-4-yl)phenyl)-N'-(2-fluoro-5-methylphenyl)urea Tolueneate Crystalline Form 1 comprising:

making N-(4-(3-amino-1H-indazol-4-yl)phenyl)-N'-(2-fluoro-5-methylphenyl)urea;

providing a mixture comprising N-(4-(3-amino-1H-indazol-4-yl)phenyl)-N'-(2-fluoro-5-methylphenyl)urea and toluene, wherein the N-(4-(3-amino-1H-indazol-4-yl)phenyl)-N'-(2-fluoro-5-methylphenyl)urea is completely dissolved in the toluene;

causing N-(4-(3-Amino-1H-indazol-4-yl)phenyl)-N'-(2-fluoro-5-methylphenyl)urea Tolueneate Crystalline Form 1 to exist in the mixture, which N-(4-(3-Amino-1H-indazol-4-yl)phenyl)-N'-(2-fluoro-5-methylphenyl)urea Tolueneate Crystalline Form 1, when measured at about −100° C. in the monoclinic crystal system and $P2_1/C$ space group with radiation at 0.7107 Å, is characterized by respective lattice parameter values a, b and c of 13.80 Å±0.01 Å, 8.910 Å±0.007 Å and 19.87 Å±0.02 Å and respective $\alpha$, $\beta$ and $\gamma$ values of about 90°, 103.75°±0.01° and 90°; and isolating the N-(4-(3-Amino-1H-indazol-4-yl)phenyl)-N'-(2-fluoro-5-methylphenyl)urea Tolueneate Crystalline Form 1.

Still another embodiment comprises N-(4-(3-Amino-1H-indazol-4-yl)phenyl)-N'-(2-fluoro-5-methylphenyl)urea Tolueneate Crystalline Form 1 prepared by the process of the preceeding embodiment.

In a process for making N-(4-(3-Amino-1H-indazol-4-yl)phenyl)-N'-(2-fluoro-5-methylphenyl)urea Tolueneate Crystalline Form 1 comprising reacting an acid or diacid salt of N-(4-(3-amino-1H-indazol-4-yl)phenyl)-N'-(2-fluoro-5-methylphenyl)urea and a base and crystallization or recrystallization of N-(4-(3-Amino-1H-indazol-4-yl)phenyl)-N'-(2-fluoro-5-methylphenyl)urea Tolueneate Crystalline Form 1 from toluene, still another embodiment of this invention comprises crystallizing or recrystallizing the N-(4-(3-Amino-1H-indazol-4-yl)phenyl)-N'-(2-fluoro-5-methylphenyl)urea Tolueneate Crystalline Form 1 from a solid, semisolid, wax or oil form of N-(4-(3-amino-1H-indazol-4-yl)phenyl)-N'-(2-fluoro-5-methylphenyl)urea that is mixed with one or more than one solvent from the deprotonation reaction.

Still another embodiment comprises N-(4-(3-amino-1H-indazol-4-yl)phenyl)-N'-(2-fluoro-5-methylphenyl)urea Tolueneate Crystalline Form 1 prepared by the process of the preceeding embodiment.

Still another embodiment comprises ABT-869 for use in preparing N-(4-(3-Amino-1H-indazol-4-yl)phenyl)-N'-(2-fluoro-5-methylphenyl)urea Tolueneate Crystalline Form 1.

Still another embodiment comprises a salt of ABT-869 for use in preparing N-(4-(3-Amino-1H-indazol-4-yl)phenyl)-N'-(2-fluoro-5-methylphenyl)urea Tolueneate Crystalline Form 1.

Still another embodiment comprises the hydrochloride salt of ABT-869 for use in preparing N-(4-(3-Amino-1H-indazol-4-yl)phenyl)-N'-(2-fluoro-5-methylphenyl)urea Tolueneate Crystalline Form 1.

DETAILED DESCRIPTION OF THE INVENTION

This invention pertains to discovery of N-(4-(3-amino-1H-indazol-4-yl)phenyl)-N'-(2-fluoro-5-methylphenyl)urea Tolueneate Crystalline Form 1, ways to make it and ways to use it.

The terms "N-(4-(3-amino-1H-indazol-4-yl)phenyl)-N'-(2-fluoro-5-methylphenyl)urea" and "ABT-869" are meant to be used interchangeably.

The terms "ABT-869" and "an ABT-869" without any indicia of crystallinity or non-crystallinity associated with it, as used herein, mean amorphous ABT-869, a crystalline ABT-869, microcrystalline ABT-869, ABT-869 in solution, a semi-solid, wax or oil form of ABT-869, mixtures thereof and the like.

The terms "crystalline" and "microcrystalline," as used herein, mean having a regularly repeating arrangement of molecules which is maintained over a long range or external face planes.

Unless stated otherwise, percentages herein are weight/weight (w/w) percentages.

The term "hydrochloride salt," as used herein, means having associated therewith one or more than one hydrochloride equivalent.

The term "solvent," as used herein, means a liquid in which a compound is soluble or partially soluble enough at a given concentration to dissolve or partially dissolve the compound.

The term "anti-solvent," as used herein, means a liquid in which a compound is insoluble enough at a given concentration to be effective for precipitating that compound from a solution.

Solvents and anti-solvents may be mixed with or without separation of phases.

It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

The term "acid," as used herein, means a compound having at least one acidic proton. Examples of acids for the practice of this invention include, but are not limited to, hydrochloric acid, hydrobromic acid, trifluoroacetic acid, trichloroacetic acid, sulfuric acid, phosphoric acid and the like.

The term "base," as used herein, means a compound capable of accepting a proton. Examples of bases for the practice of this invention include, but are not limited to, sodium carbonate, sodium bicarbonate, potassium carbonate, potassium bicarbonate, dibasic sodium phosphate (i.e. $Na_2HPO_4$, $K_2HPO_4$ and the like), triethylamine, diisopropylethylamine and the like.

Causing ABT-869 Tolueneate Crystalline Form 1 to exist in a mixture comprising ABT-869 and toluene, wherein the ABT-869 has completely dissolved, is known as nucleation.

For the practice of this invention, nucleation may be made to occur by means such as solvent removal, temperature change, solvent-miscible anti-solvent addition, solvent-immiscible anti-solvent addition, chafing or scratching the interior of the container, preferably a glass container, in which nucleation is meant to occur with an implement such as a glass rod or a glass bead or beads, or a combination of the foregoing.

For the practice of this invention, nucleation may be followed by crystal growth, accompanied by crystal growth, or followed and accompanied by crystal growth during which, and as a result of which, the percentage of ABT-869 Tolueneate Crystalline Form 1 in toluene increases.

The term "isolating" as used herein, means separating ABT-869 Tolueneate Crystalline Form 1 from solvent, anti-solvent, or a mixture of solvent anti-solvent. This is typically accomplished by means such as centrifugation, filtration with or without vacuum, filtration with positive pressure, distillation, evaporation or a combination thereof.

Preparation of ABT-869 and its utility as a PTK inhibitor is described in commonly-owned U.S. patent application Ser. No. 10/842,292, Published as 2005/0020603 A1.

Excipients for preparation of formulations made with ABT-869 Tolueneate Crystalline Form 1 to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, copovidone, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, povidone, peanut oil, potassium phosphate salts, potato starch, povidone, propylene glycol, Ringer's solution, safflower oil, sesame oil, silicon dioxide, sodium carboxymethyl cellulose, sodium phosphate salts, sodium lauryl sulfate, sodium sorbitol, sodium stearylfumarate, soybean oil, stearic acids, stearyl fumarate, sucrose, surfactants, talc, tragacanth, tetrahydrofurfuryl alcohol, triglycerides, vitamin E and derivatives thereof, water, mixtures thereof and the like.

Excipients for preparation of formulations made with ABT-869 Tolueneate Crystalline Form 1 to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like.

Excipients for preparation of formulations made with ABT-869 Tolueneate Crystalline Form 1 to be administered osmotically include, for example, chlorofluorohydrocarbons, ethanol, water, mixtures thereof and the like.

Excipients for preparation of formulations made with ABT-869 Tolueneate Crystalline Form 1 to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like.

Excipients for preparation of formulations made with ABT-869 Tolueneate Crystalline Form 1 to be administered rectally or vaginally include, but are not limited to, cocoa butter, polyethylene glycol, wax, mixtures thereof and the like.

The following example is presented to provide what is believed to be the most useful and readily understood description of procedures and conceptual aspects of this invention.

EXAMPLE 1

Preparation of ABT-869 Tolueneate Crystalline Form 1

This example was prepared by recrystallizing ABT-869 from toluene at about 110° C. and filtering.

The term "about" preceding a temperature means the given temperature ±5° C.

The foregoing is meant to be illustrative of the invention and not intended to limit it to the disclosed embodiments. Variations and changes obvious to one skilled in the art are intended to be within the scope and nature of the invention as defined in the claims.

I claim:

1. N-(4-(3-Amino-1H-indazol-4-yl)phenyl)-N'-(2-fluoro-5-methylphenyl) urea Tolueneate Crystalline Form 1 which, when measured at about −100° C. in the monoclinic crystal system and $P2_1/C$ space group with radiation at 0.7107 Å, is characterized by respective lattice parameter values a, b and c of 13.80Å±0.01Å, 8.910Å±0.007Å and 19.87Å±0.02Å and respective α, β and γ values of about 90°, 103.75°±0.01° and 90°.

2. A process for making N-(4-(3-Amino-1H-indazol-4-yl)phenyl)-N'-(2-fluoro-5-methylpheny) urea Tolueneate Crystalline Form 1 comprising:

providing a mixture comprising N-(4-(3-amino-1H-indazol-4-yl)phenyl)-N'-(2-fluoro-5-methylpheny)urea and toluene, wherein the N-(4-(3-amino-1H-indazol-4-yl)

phenyl)-N'-(2-fluoro-5-methylpheny)urea is completely dissolved in the toluene; and causing N-(4-(3-Amino-1H-indazol-4-yl)phenyl)-N'-(2-fluoro-5-methylpheny)urea Tolueneate Crystalline Form 1 to exist in the mixture, which N-(4-(3-Amino-1H-indazol-4-yl)phenyl)-N'-(2-fluoro-5-methylpheny)urea Tolueneate Crystalline Form 1, when measured at about −100°C. in the monoclinic crystal system and P$2_1$/C space group with radiation at 0.7107 Å, is characterized by respective lattice parameter values a, b and c of 13.80Å±0.01Å, 8.910Å±0.007Å and 19.87Å±0.02Å and respective α, β and γ values of about 90°, 103.75°±0.01° and 90°.

3. The process of claim 2 further comprising isolating the N-(4-(3-Amino-1H-indazol-4-yl)phenyl)-N'-(2-fluoro-5-methylpheny)urea Tolueneate Crystalline Form 1.

* * * * *

UNITED STATES PATENT AND TRADEMARK OFFICE
CERTIFICATE OF CORRECTION

PATENT NO. : 7,943,782 B2
APPLICATION NO. : 12/251964
DATED : May 17, 2011
INVENTOR(S) : Michael J. Rozema Page 1 of 1

It is certified that error appears in the above-identified patent and that said Letters Patent is hereby corrected as shown below:

Cover Page, item [75] Inventor, remove "Rodger F. Henry" replace with --Michael J. Rozema--

Column 5 part of Claim 2, Line 4, revise "fluoro-5-methylpheny)urea" to read as --fluoro-5-methylphenyl)urea--

Column 5 part of Claim 2, Line 6, revise "(2-fluoro-5-methylpheny)" to read as --(2-fluoro-5-methylphenyl)--

Column 6 part of Claim 3, Line 7, revise "methylpheny)" to read as --methylphenyl)--

Signed and Sealed this
First Day of January, 2013

David J. Kappos
*Director of the United States Patent and Trademark Office*